United States Patent

Eaton et al.

[11] 4,069,380
[45] Jan. 17, 1978

[54] TRIAZINE COMPOSITIONS

[75] Inventors: David Crawford Eaton; Benjamin Eric Nicholson; Barry Williams, all of Manchester, England

[73] Assignee: Imperial Chemical Industries Limited, London, England

[21] Appl. No.: 720,392

[22] Filed: Sept. 3, 1976

[30] Foreign Application Priority Data

Sept. 24, 1975 United Kingdom ............ 39133/75

[51] Int. Cl.$^2$ ............ C07D 251/46; C07D 251/52
[52] U.S. Cl. ............ 544/212; 544/209
[58] Field of Search ............ 260/249.5, 248 CS, 249.8

[56] References Cited

U.S. PATENT DOCUMENTS

| | | |
|---|---|---|
| 3,454,551 | 7/1969 | Mangini et al. ............ 260/249.5 X |
| 3,847,915 | 11/1974 | Bishop et al. ............ 260/249.5 X |
| 3,962,241 | 6/1976 | Hunter ............ 260/249.5 |

Primary Examiner—John M. Ford
Attorney, Agent, or Firm—Cushman, Darby & Cushman

[57] ABSTRACT

Condensation products of cyanuric chloride, resorcinol and ammonia of the formula:

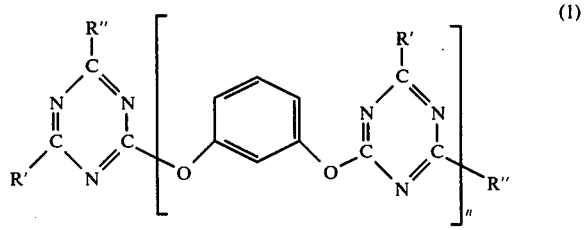

in which $n$ is an integer; each $R'$ is independently $NH_2$ or Cl and each $R''$ is independently $NH_2$ or

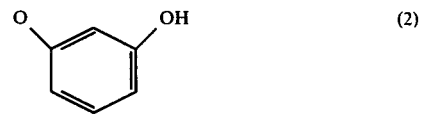

provided that a sufficient number of radicals represented by $R'$ are Cl atoms to provide a chlorine content of at least 3% by weight and at least one of $R'$ and $R''$ is $NH_2$; their manufacture and their use as promoters of bond strength between rubber and copper or its alloys. Of particular use in connection with brass-coated steel cords in motor tires.

5 Claims, No Drawings

TRIAZINE COMPOSITIONS

This invention relates to new triazine derivatives, compositions containing the same, their manufacture, and their use for bonding of rubber to copper or copper alloys.

U.S. Pat. No. 3,894,903 describes and claims a method of bonding a rubber to copper and alloys thereof which comprises adding to a vulcanisable rubber composition a triazine compound of the formula:

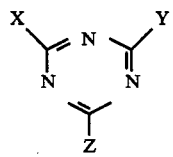

wherein X is a group containing a phenolic hydroxyl group and derived by loss of one hydrogen atom from a dihydroxybenzene, aminophenol or mercaptophenol any of which may contain as substituent a chlorine or bromine atom, an alkyl or alkoxy group containing from 1 to 4 carbon atoms or another hydroxyl or amino group, and Y and Z, which may be the same or different, may be a group of the type represented by X or a hydrogen or chlorine atom or a hydroxy, amino or mercapto group in which the hydrogen atom or atoms may optionally be substituted by an alkyl group containing from 1 to 12 carbon atoms, a cycloalkyl group, an alkenyl group containing from 3 to 12 carbon atoms, a phenyl group optionally substituted by a chlorine atom or alkyl or alkoxy group containing from 1 to 4 carbon atoms, or in the case where Y and/or Z represents a substituted amino group such substituent may take the form of a divalent radical forming a five or six-membered ring with the nitrogen atom, and bringing the vulcanisable rubber composition into contact with the copper or alloy thereof, and heating the composite article to vulcanize the rubber.

It has now been found that certain other condensation products of cyanuric chloride, resorcinal and ammonia are of value as bonding agents in this connection.

The condensation products of the present invention are represented by the formula:

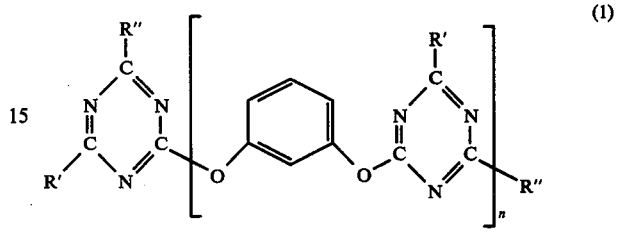

in which $n$ is an integer; each R' is independently $NH_2$ or Cl and each R" is independently $NH_2$ or

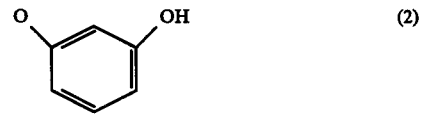

provided that a sufficient number of radicals represented by R' are Cl atoms to provide a chlorine content of at least 3% by weight and at least one of R' and R" is $NH_2$.

The condensation products of the invention may be substantially pure compounds, e.g. compounds of formulae:

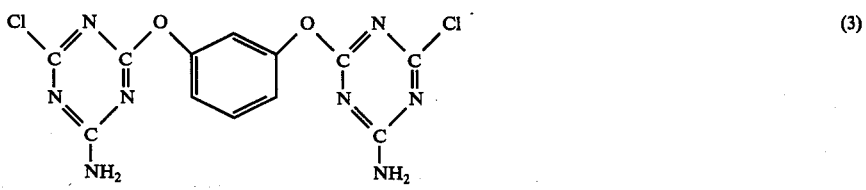

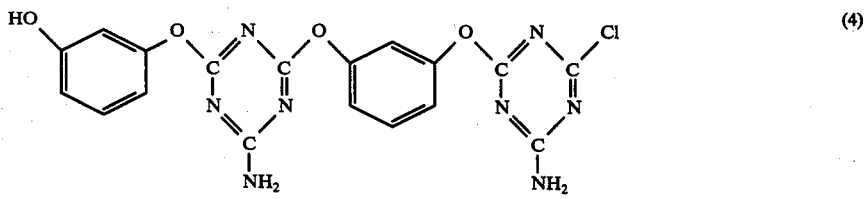

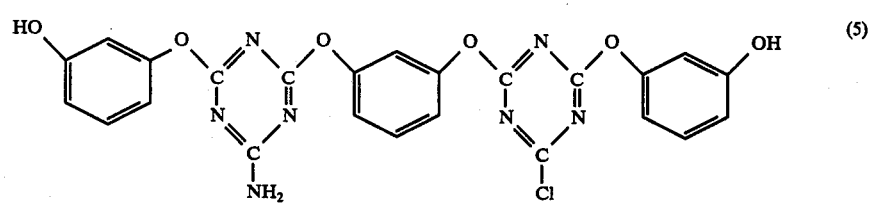

or

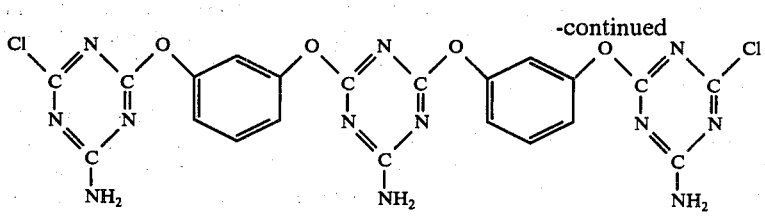 (6)

or mixtures of these and other related linear compounds or possibly cyclic compounds, obtained by condensation of cyanuric chloride with resorcinol and ammonia e.g. of the formula:

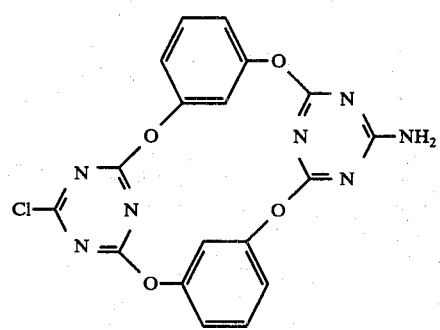 (7)

The new triazine compounds and the mixtures containing them can be obtained by condensing together cyanuric chloride, resorcinol and ammonia, the proportions, order of reaction and reaction conditions being varied according to the final product desired.

Thus the compound of formula (3) above is obtained by reacting two moles of cyanuric chloride with one mole of resorcinol at 0°–5° C and reacting the resultant product with two moles of ammonia at 35° C.1 On the other hand, the compound of formula (4) is obtained by reacting one mole of cyanuric chloride with one mole of ammonia to form amino dichloro-s-triazine, separately reacting a second mole of cyanuric chloride with two moles of resorcinol and reacting the resulting product at 50°–55° C, with the amino dichloro-s-triazine.

However, preferred compositions which are mixtures comprising one or more compounds of formula (1) can be obtained in a simple manner by reacting cyanuric chloride in an aqueous medium with from 0.5 to 1.1 moles of resorcinol in a first stage and when reaction is complete, partially replacing the residual chlorine atms by amino groups by reacting with ammonia.

The first stage is preferably carried out at a temperature of from −5° to 20° C, more especially at from 0° to 5° C, in the presence of an acid-binding agent to neutralise the liberated hydrogen chloride. Whereas in the reaction of phenolic compounds with cyanuric chloride it is usually found preferable to use caustic soda or other highly alkaline compounds as acid-binding agent, it is surprisingly found with resorcinol that reaction is preferably carried out at a pH of from 6–7, and acid-binding agents, e.g. alkali-metal bicarbonates, providing that such a pH are preferred. The rate of reaction can be followed in the usual way by measuring the amount of chloride ion which has been liberated during the course of the reaction.

When reaction of the resorcinol is substantially complete, the second stage of the reaction may be carried out by adding aqueous ammonia to the reaction mixture and raising the temperature to effect further reaction. It is preferred to use an excess of ammonia, to act as acid-binding agent, and even higher amounts than that required in this capacity are found to be useful in obtaining products completely free from traces of unreacted cyanuric chloride. Thus, the use of at least 3 preferably 4 or more moles, of ammonia/mole of cyanuric chloride is preferred.

The reaction products are insoluble in water and can be separated by filtration and dried. Preferably an alkaline earth metal hydroxide or carbonate is added to act as stabiliser.

As noted above, the new triazine derivatives and mixtures containing them are of value for the bonding of rubber to copper or to copper alloys.

Thus the invention also provides a method of bonding a rubber to copper or alloys thereof, which comprises introducing into a vulcanisable rubber composition one or more condensation products of formula (1) wherein $n$, $R'$ and $R''$ have the meanings stated above, possibly in admixture with other compounds obtained by condensation of cyanuric chloride with resorcinol and ammonia, thereafter bringing the vulcanisable rubber composition into contact with the copper or alloy thereof, and after heating the composite article to vulcanise the rubber.

The rubber may be natural rubber or a vulcanisable synthetic rubber such as polymers including cis-polymers of butadiene and isoprene, polychlorobutadiene, and copolymers of dienes such as butadiene and isoprene with polymerisable compounds such as styrene, isobutene, acrylonitrile, and methyl methacrylate and terpolymers such as ethylene/propylene/diolefin, and blends of these rubbers.

The invention is of particular value in promoting bonding of rubber to brass-coated steel cords since these are used to reinforce tyres and without a bonding agent they do not adhere strongly to the rubber. The invention is however also of use in promoting bonding to other copper articles and articles of copper alloys such as engine mountings, shock absorbers, plant linings and metal reinforced hose.

The triazine derivative should be used in amount at least 0.1%, and preferably between 1 and 5%, of the weight of rubber. It is not necessary that the triazine derivative should be distributed throughout the rubber but only that it should be present in adequate amount at the rubber/metal interface. Thus comparatively small amounts of a rubber containing the triazine derivative may be used as a bonding agent at the point of contact between metal and a rubber free from the triazine derivative.

Vulanisation may be carried out by heating the composite article to a temperature conventionally used for vulcanising the vulcanisable rubber composite concerned. The vulcanisable rubber composition will normally contain a vulcanising agent such as sulphur or a sulphur donor for example N,N'-dithio-bis(hexahydro-2H-acepinone-2), 4,4'-dithiomorpholine or bis-(diethyl thiophosphoryl)trisulphide and a vulcanisation accelerator for example benzothiazylsulphenamides such as benzothiazyl-2-cyclohexyl sulphenamide, 2-(morpholinothio)benzothiazole, benzothiazyl-2-dicyclohexyl sulphenamide, and N-t-butyl-2-benzothiazolesulphenamide, 2-mercaptobenzothiazole, 2-mercaptobenzothiazyl-disulphide, diarylguanidines, thiurams and dithiocarbamates.

The vulcanisable rubber composition may if desired contain other conventional rubber adjuvants such as antioxidants, antiozonants, fillers, reinforcing agents, pigments, processing oils and accelerator activators such as zinc oxide and stearic acid and also ingredients used in other bonding systems such as formaldehyde generators.

The invention is illustrated but not limited by the following Examples in which all parts and percentages are by weight unless otherwise stated.

EXAMPLE 1

A slurry of water (310 parts), resorcinol (28.6 parts) and sodium bicarbonate (32.8 parts) is prepared. This slurry is added with stirring to a suspension of cyanuric chloride (48 parts) and dispersing agent (0.5 parts) in ice-water mixture (260 parts) maintaining the temperature at 0° to 5° C. After 3 hours ammonia liquor (19.9 parts at 100%) is added, with stirring continuing, and the temperature raised to 35°-37° C and held for 2½ hours. 3 parts of lime are added and the product is isolated by filtration, washed with water and dried. 59 parts of a white powder are obtained.

EXAMPLE 2

A solution of cyanuric chloride (36.9 parts) in acetone (200 parts) at 0° C was prepared. To this solution was added with stirring at 0°-5° C a solution of resorcinol (11 parts) and sodium hydroxide (8 parts) in water (100 parts) dropwise over 30 minutes. The reaction was stirred for a further 45 minutes at 0°-5° C. Concentrated ammonia solution (14 parts at 100%) was added dropwise with stirring over 45 minutes and stirring continued for a further 2 hours at 5°-10° C. The reaction temperature was raised to 35° C and held for 1 hour. The product was isolated by filtration, washed with water and dried. The product was obtained as a white powder containing 1,3-bis(2'-amino-4'-chloro-s-triazinyl-6'-oxy)benzene as the main constituent. Found: C, 40.4; H 23; N 29.5 and Cl 14.8%. $C_{12}H_8Cl_2N_8O_2$ requires C 39.25; H 2.2; N 30.5 and Cl 19.35%.

EXAMPLE 3

A solution of 20.8 parts of 2,4-bis(m-hydroxyphenoxy)-6-amino-s-triazine in 6.07 parts of triethylamine and 280 parts of acetone was added dropwise over about 30 minutes at room temperature with stirring to a mixture of 11 parts of 2-amino-4,6-dichloro-s-triazine in 40 parts of acetone. After the addition was complete stirring was continued and the reaction heated to 50°-55° C and held for 3.5 hours. The reaction was then cooled and poured into 800 parts of ice-cold water with vigorous agitation. The precipitated product was isolated by filtration, washed with water and dried. The product, consisting essentially of structure (4) above, was obtained as a white powder. Analysis: Found: C 50.0; H, 3.5; N 23.8; Cl 7.3%. $C_{18}H_{13}ClN_8O_4$ requires C 49.05; H 2.95; N 25.4; Cl 8.05%.

EXAMPLE 4

The procedure of Example 3 was followed except that there are used 12.14 parts of triethylamine and 22 parts of 2-amino-4,6-dichloro-s-triazine in 60 parts of acetone. The product, consisting of structure (6) above was obtained as a white powder. Analysis: Found: C 45.7; H 3.2; N 26.5; Cl 12.1. $C_{21}H_{14}Cl_2N_{12}O_4$ requires C 44.3; H 2.45; N 29.5; Cl 12.45%.

EXAMPLE 5

A suspension of 12.48 parts of 2,4-bis(m-hydroxyphenoxy)-6-amino-triazine and 7.4 parts of cyanuric chloride in 200 parts of acetone and 3.64 parts of triethylamine was stirred at 5° C for 1 hour and for a further 2 hours at room temperature. To the suspension was added dropwise with stirring over 0.25 hour at the same temperature a solution of 4.4 parts resorcinol and 3.64 parts of triethylamine in 60 parts of acetone. The reaction was then heated and stirred at 50°-55° C for 3.5 hours, cooled to 10° C and diluted with 500 parts of ice-cold water. The solid product was filtered off, washed with water and dried. The product, consisting essentially of structure (5) above was obtained as a white powder. Analysis: Found: C 51.5; H 3.6; N 19.3; Cl 6.6%. $C_{24}H_{16}ClN_7O_6$ requires C 53.95; H 3.00; N 18.35; Cl 6.65%.

EXAMPLE 6

A vulcanisable rubber composition was prepared on a two roll mill from the following ingredients:

| | |
|---|---|
| Natural rubber smoked sheets | 100 |
| Zinc oxide | 10 |
| Stearic acid | 3 |
| High Abrasion Furnace Carbon Black | 45 |
| Processing oil | 4 |
| N-dicyclohexyl-2-benzothiazyl sulphenamide | 0.7 |
| Sulphur | 4 |
| Antioxidant (acetone/diphenylamine condensate) | 1 |
| Bonding agent | as in Table 1 |

Samples measuring approximately 1¼ inch × 7/16 inch × 7.3 mm were taken from the above composition and a length of brass-coated steel cord was sandwiched between two of the samples.

The resultant sandwich was placed in a mould, and press cured for 30 minutes at 150° C. After removal from the mould the resultant block, which measured 1¼ × ½ × ½ inch, was cut into two across the cord and the force required to pull the cord out of the rubber measured.

Table 1

| Rubber in composition | 167.7 | 167.7 | 167.7 | 167.7 | 167.7 | 167.7 |
|---|---|---|---|---|---|---|
| Product of Example 1 | — | 2.0 | — | — | — | — |
| Product of Example 2 | — | — | 2.0 | — | — | — |
| Product of Example 3 | — | — | — | 2.0 | — | — |
| Product of Example 4 | — | — | — | — | 2.0 | — |
| Product of Example 5 | — | — | — | — | — | 2.0 |
| Force (Kg) required to pull cord from 1¼" long block | 50 56 | 60 — | 61 — | — 65 | — 64 | — 61 |

What we claim is:
1. A condensation product of cyanuric chloride, resorcinol and ammonia consisting primarily of a compound of the formula

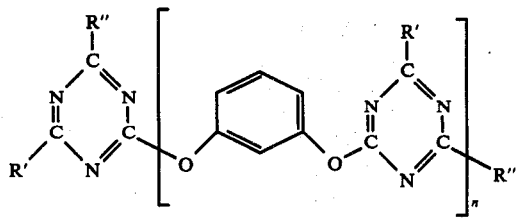
(1)

in which n is 1 or 2; each R' is independently NH₂ or Cl and each R" is independently NH₂ or

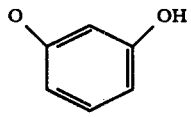
(2)

provided that a sufficient number of radicals represented by R' are Cl atoms to provide a chlorine content of at least 3% by weight and at least one of R' and R" is NH₂.

2. A condensation product as claimed in claim 1 having the formula:

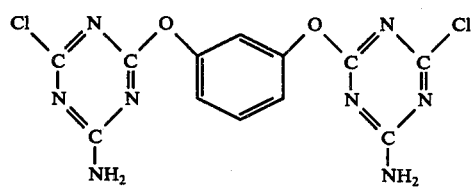
(3)

3. A condensation product as claimed in claim 1 having the formula:

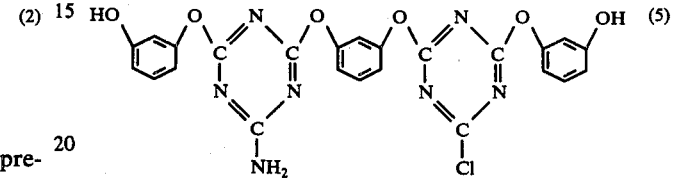
(4)

4. A condensation product as claimed in claim 1 having the formula:

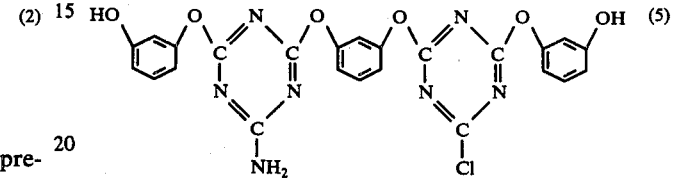
(5)

5. A condensation product as claimed in claim 1 having the formula:

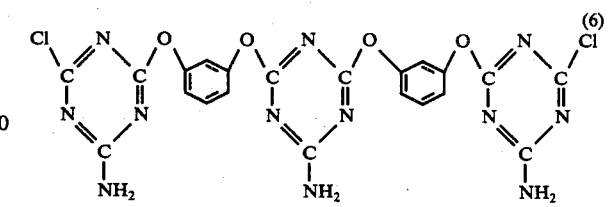
(6)

* * * * *